| United States Patent [19] | [11] Patent Number: 4,877,617 |
|---|---|
| Namikoshi et al. | [45] Date of Patent: Oct. 31, 1989 |

[54] FUNGICIDAL AND BACTERICIDAL METHOD

[75] Inventors: Hajime Namikoshi; Tatsuo Goto, both of Himeji, Japan

[73] Assignee: Daicel Chemical Industries Ltd., Osaka, Japan

[21] Appl. No.: 939,704

[22] Filed: Dec. 9, 1986

[30] Foreign Application Priority Data

Dec. 11, 1985 [JP] Japan ................................. 60-278454
Dec. 11, 1985 [JP] Japan ................................. 60-278455

[51] Int. Cl.$^4$ ...................... A61K 31/70; A01N 25/34
[52] U.S. Cl. .................................... 424/409; 424/411; 523/122; 428/907; 536/3; 536/98
[58] Field of Search ...................... 428/907; 536/98, 3; 424/409, 411; 523/122

[56] References Cited

U.S. PATENT DOCUMENTS

| 2,881,074 | 4/1959 | Hardwood | 514/57 |
| 3,283,357 | 11/1966 | Decker et al. | 424/411 |
| 4,007,258 | 2/1977 | Cohen et al. | 424/409 |
| 4,529,398 | 7/1985 | Wong et al. | 424/411 |
| 4,617,385 | 10/1986 | Namikoshi et al. | 536/98 |
| 4,708,870 | 11/1987 | Pardini | 523/122 |

FOREIGN PATENT DOCUMENTS 1103336 3/1961 Fed. Rep. of Germany .
2169805 7/1986 United Kingdom ................ 424/411

OTHER PUBLICATIONS

Unexamined Japanese Patent Publication Sho 59-187001.
Duetsche Apotheker–Zeitung, vol. 106, No. 35, pp. 1206–1208, 1966.
Bokin-bobai, *Protection Against Bacteria and Fungi*, vol. 7, No. 11, pp. 7–14, 1979.
Bokin-bobai, Protection Against Bacteria and Fungi, vol. 12, No. 11, pp. 56–571, 1984.
Pharma. Ind., vol: 37, No. 2, p. 100, 1985.

*Primary Examiner*—Ronald W. Griffin
*Attorney, Agent, or Firm*—Bryan, Cave, McPheeters & McRoberts

[57] ABSTRACT

A fungicidal and bactericidal method of imparting fungicidal and bactericidal properties to an article by coating or impregnating the article with a solution of a quaternary ammonium salt of alginic acid or carboxymethyl cellulose (which is insoluble or sparingly soluble in water) in an organic solvent and thereafter removing the solvent from the article.

6 Claims, No Drawings

FUNGICIDAL AND BACTERICIDAL METHOD

BACKGROUND OF THE INVENTION

1. Field of the Invention

The present invention relates to a fungicidal and bactericidal method employing organic solvent solutions of fungicidal and bactericidal quaternary ammonium salts which are insoluble or sparingly soluble in water.

2. Description of the Prior Art

Various devices, appliances and equipment for household uses, industrial uses and medicinal uses widely suffer from contamination of microorganisms, for example, due to the growth of fungi or harmful bacteria, or from deterioration of the constituent material, irrespective of whether they are made of inorganic or organic materials.

The fungicidal and bactericidal methods heretofore used to overcome this problem predominantly employ water-soluble fungicidal or bactericidal agents, so that these agents are dissolved out with water such as rainwater, failing to fully protect devices and equipment from growth of fungi and harmful bacteria. It is therefore strongly required to provide effective measures.

The present invention, which has been accomplished to fulfill the above requirement, provides a method which employs a fungicidal and bactericidal quaternary ammonium salt of alginic acid or carboxymethylcellulose (hereinafter referred to as "CMC") as dissolved in an organic solvent, the salt being sparingly soluble or insoluble in water. As to such salts, the following compounds and methods are known.

(a) Quaternary ammonium salts of alginic acid (i) Unexamined Japanese Patenet Publication SHO 59-187001 discloses a method of preparing water-insoluble film like acid polysaccharides wherein an aqueous solution of benzalkonium chloride of a quaternary ammonium compound is gently added to an aqueous solution of sodium alginate to form a water-insoluble thin film of benzalkonium salt of alginic acid at the interface between the two solutions. However, the publication discloses nothing about the use of the quaternary ammonium salt of alginic acid for coating or impregnation as disclosed in the present invention, nor does it mention anything about the solubility of such salts in organic solvents.

(ii) West German Pat. No. 1,103,336 discloses the dimethyl lauryl cetyl ammonium salt, abietyl ammonium salt and laurylpyridinium salt of alginic acid, while Deutsche Apotheker-Zeitung, Vol. 106, No. 35, pp 1206–1208, 1966 discloses the dodecyl methyl 3,4-dichlorobenzyl ammonium salt of alginic acid, but these publications disclose nothIng about method such as that of the present invention.

(b) Quaternary ammonium salts of CMC

"Bokin-bobi (Protection against Bacteria and Fungi)," Vol. 7, No. 11, pp. 7–14, 1979 and the same, Vol. 21, No. 11, pp. 561–571, 1984 disclose that a quaternary ammonium compound such as benzalkonium chloride, cetyl trimethyl ammonium bromide, cetyl pyridinium chloride, lauryl pyridinium chloride, dimethyl phenyl benzyl ammonium chloride or tetradecyl dimethyl benzyl ammonium chloride is fixed to CMC serving as a carrier to pass a liquid through the resulting layer for sterilization. Nevertheless, a method such as that of the present invention is not disclosed in these publications.

Furthermore, the dimethyl lauryl cetyl ammonium salt of CMC is disclosed in West German Patent No. 1,103,336, the trimethyl octadecyl ammonium salt of CMC in U.S. Pat. No. 2,881,074, the dodecyl dimethyl 3,4-dichlorobenzylammonium salt of CMC in Deutsche Apotheker-Zeitung, Vol. 106, No. 35, pp. 1206–1208, 1966, and the cetyl trimethylammonium salt of CMC in Pharm. Ind., Vol. 37, No. 2, p. 100, 1975. However, these publications suggest nothing about the method of the present invention.

These quaternary ammonium salts of CMC are used to utilize the characteristics of CMC as a high-molecular-weight substance and also the characteristics of the quaternary ammonium group. Since the starting material CMC for these quaternary ammonium salts of CMC is not specifically disclosed as to the degree of substitution (hereinafter referred to briefly as "DS") of carboxymethyl group per anhydrous glucose unit of CMC, the DS is thought to be less than 1.0 as is generally the case with commercial products. It therefore follows that less than 1.0 molecule of quaternary ammonium moiety can be present per glucose unit since the quaternary ammonium group combines with the carboxymethyl group of CMC in the molecular ratio of 1:1. Thus, a larger amount of quaternary ammonium moiety is not usable to utilize its properties. These known quaternary ammonium salts of CMC are generally soluble in water (insoluble in organic solvents) when the quaternary ammonium moiety has a low molecular weight. However, when the quaternary ammonium moiety has an increased molecular weight, such salts are insoluble in water and are not fully soluble in polar solvents such as alcohol and acetone or non-polar solvents such as toluene. It is therefore difficult to use these salts in the form of an organic solvent solution.

SUMMARY OF THE INVENTION

The present invention provides a method of imparting fungicidal and bactericidal properties to an article by coating or impregnating the article with a solution of a fungicidal and bactericidal quaternary ammonium salt in an organic solvent or a mixture of the organic solvent and a small amount of water and thereafter removing the organic solvent from the article, the quaternary ammonium salt being insoluble or sparingly soluble in water and represented by the formula (I)

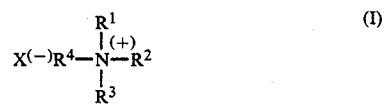

wherein $X^{(-)}$ is a group formed by removing a hydrogen ion from at least one carboxyl group of alginic acid or carboxymethylcellulose having 1.5–3.0 as the degree of substitution by carboxymethyl group per anhydrous glucose unit; and $R^1$ to $R^4$ are each a $C_{1-20}$ straight-chain or branched saturated or unsaturated aliphatic hydrocarbon group, three of $R^1$ to $R^4$ are each the hydrocarbon group and the remaining one is an aralkyl group, a trialkylammoniumalkyl group or an aryloxyalkyl group, two of $R^1$ to $R^4$ are each the hydrocarbon group and the remaining two are an aralkyl group, a dialkylphenoxy- or alkylphenoxyalkyleneoxyalkyl group, or one or two of $R^1$ to $R^4$ are the hydrocarbon group and the remaining two or three form a heterocyclic ring together with the nitrogen atom.

DESCRIPTION OF THE PREFERRED EMBODIMENTS

The quaternary ammonium salts of the foregoing formula (I) are used in the present invention.

Examples of the quaternary ammonium group in the quaternary ammonium salt (I) include:

(i) Those wherein $R^1$ to $R^4$ are each a $C_{1-20}$ straight-chain or branched saturated or unsaturated aliphatic hydrocarbon group, specifically, lauryl trimethyl ammonium, cetyl trimethyl ammonium, stearyl trimethyl ammonium, trioctyl methyl ammonium, dimethyl distearyl ammonium, dimethyl oleyl linoleylammonium, trimethyl monobehenyl ammonium, methyl trilauryl ammonium, etc.

(ii) Those wherein three of $R^1$ to $R^4$ are each the above hydrocarbon group and the remaining one is an aralkyl group, trialkyl ammonium alkyl group or aryloxyalkyl group, specifically, tetradecyl dimethyl benzyl ammonium, (trimethylammoniumhexyl)trimethyl ammonium, (trimethylammoniumdecyl)trimethyl ammonium [i.e., decamethonium], lauryl phenoxyethyl dimethyl ammonium etc.

(iii) Those wherein two of $R^1$ to $R^4$ are each the above hydrocarbon group and the remaining two are an aralkyl group and a mono- or di-alkylphenoxyalkyleneoxyalkyl group, specifically, diisobutylphenoxyethyoxyethyl dimethyl benzyl ammonium [i.e., benzethonium], (diisobutyl)methylphenoxyethyoxyethyl dimethyl benzyl ammonium [i.e., methylbenzethonium], etc.

(iv) Those wherein one or two of $R^1$ to $R^4$ are the above hydrocarbon group and the remaining two or three form a heterocyclic ring together with the nitrogen atom, specifically laurylpyridinium, cetylpyridinium, laurylisoquinolinium, laurylnicotinium, laurylquinaldinium, etc.

Preferred exwmples of the quaternary ammonium group are tetradecyl dimethyl benzyl ammonium, dodecyl trimethyl ammonium, cetylpyridinium, benzethonium and methylbenzethonium groups.

Besides, the quaternary ammonium groups as mentioned above may be in a mixture from the veiwpoints of commercial availability or easiness on preparation.

Alginic acid which constitutes the quaternary ammonium salts of the present invention may be one commercially available and having a molecular weight, for example, of 10,000 to 500,000, and may be in the form of salt. Examples of useful alginates are alkali metal salts such as sodium salt and potassium salt, alkaline earth metal salts such as calcium salt, etc. Usually, the sodium salt is desirable.

CMC constituting the quaternary ammonium salt of the invention must be 1.5 to 3.0 in DS in view of the solubility of the salt in organic solvents. Usable as CMC with such a high DS is, for example, one produced by the multistage etherification process disclosed in Unexamined Japanese Patent Publication SHO 58-176202. CMC is used usually in the form of an alkali metal salt such as sodium salt or potassium salt. Although alkaline earth metal salts, such as calcium salt, of CMC, and CMC in the form of an acid or partial acid are usable, the sodium salt is most preferable.

Besides, the CMC can be represented by the following formula:

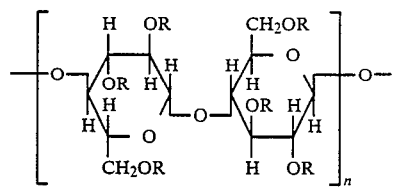

wherein R is a hydrogen atom or a carboxymethyl group, n is 10 to 1000, and the DS by the carboxymethyl group is 1.5 to 3.0 per anhydrous glucose unit.

The quaternary ammonium salt of alginic acid to be used in the present invention may be prepared by reacting alginic acid or a salt thereof with an appropriate quaternary ammonium compound in contact therewith, collecting the resulting precipitate by filtration, washing the precipitate and drying the same at a reduced pressure at room temperature. For this reaction, at least one of the reactants is used in the form of a solution.

It is especially desirable for this reaction to add the quaternary ammonium compound or a solution thereof to an aqueous solution of alginate. Usually, the reaction can be conducted easily at or around room temperature.

It is also desirable to use the equivalent amount or an excess of the quaternary ammonium compound based on the carboxyl groups of aliginic acid to be reacted therewith, whereby the quaternary ammonium group can be introduced into the alginic acid to the greatest possible extent to afford strong fungicidal and bactericidal properties. When required, however, the quaternary ammonium compound may be used in an amount smaller than the equivalent amount.

On the other hand, the quaternary ammonium salt of CMC to be used in the present invention is prepared by mixing an aqueous solution of CMC which is 1.5 to 3.0 in DS by carboxymethyl per anhydrous glucose unit or of a salt thereof, with an appropriate quaternary ammonium compound or a solution thereof for reaction, and separating off and purifying the resulting quaternary ammonium salt of CMC.

The organic solvent to be used in the present invention is preferably one easily dissolving the foregoing quaternary ammonium salts and having a lower boiling point. Depending on the quaternary ammonium salt to be dissolved and on the use thereof, suitable solvent are selected which include, for example, methanol, ethanol, isopropanol and like lower alkyl alcohols, acetone, benzene, toluene etc.

Depending on the kind of the quaternary ammonium salt, a mixture of an organic solvent and a small amount of water may be used as the solvent.

The concentration of the quaternary ammonium salt in the organic solvent is usually about 0.01 to about 30 (W/V)%, although the concentration is dependent on the desired fungicidal and bactericidal properties of the coating or the impregnated material.

According to the present invention, articles such as device, appliance, equipment or the like to be given fungicidal and bactericidal properties is coated with a solution of the quaternary ammonium salt in such an organic solvent, and the solvent is removed by a usual method as by drying to form a surface coating of the quaternary ammonium salt. Alternatively, the material to be given fungicidal and bactericidal properties is impregnated with the solution, followed by the removal of the solvent in the same manner as above.

The articles to be thus coated include surfaces covered with a coating composition or uncoated surfaces, for example, of glass and plastics, such as the inner wall of containers for pure water, inner wall of bathrooms exposed to a high humidity and prone to the growth of fungi and inner wall of reinforced concrete houses which is susceptible to the condensation of water vapor especially during winter. It is also possible to admix the quaternary ammonium salt or the solution thereof with a coating composition to be applied to these surfaces.

The articles to be impregnated with the organic solvent solution of quaternary ammonium salt include any of materials which can be impregnated with the solution, such as paper, fibers, nonwoven fabrics, leather, sponge, rattan, wood, etc. More specifically, the articles include those which are usually not washed frequently or are difficult wash, such as thick bedclothes, tatami or straw matting, wallpaper, wainscot, sporting goods (balls for volleyball or basketball, gloves for baseball, protectors for Japanese fencing, etc.), furniture and furnishings including chests of drawers, porous heat insulators, filters, books, documents, shoes, etc.

The present invention will be described in greater detail with reference to the following preparation examples, examples and fungicidal or bactericidal tests, which nevertheless in on way limit the scope of the invention.

In the below Examples, the solvents used are analytically pure and do not substantially contain water, as far as any specific attention to water content is not made.

PREPARATION EXAMPLE 1

Preparation of quaternary ammonium salts of alginic acid

To 200 g of about 2 W/V % aqueous solution of sodium alginate was added at room temperature about 10% aqueous solution of the quaternary ammonium compounds given below, in an amount equivalent to the carboxyl group, followed by stirring. The resulting precipitate was filtered off, thoroughly washed with water and dried in a vacuum at room temperature. In this way, the quaternary ammonium salts of alginic acid listed in Table 1 were prepared.

(1) Sodium alginate used
Duckalgin NSPM from Kamogawa Kasei Co., Ltd. (Japan)
(2) Quaternary ammonium compounds used
Dodecyl trimethyl ammonium chloride
Tetradecyl dimethyl benzyl ammonium chloride
Cetyl pyridinium chloride
Benzethonium chloride
Methylbenzethonium chloride Table 1 shows the solubilities of the salts in solvents.

TABLE 1

| Quaternary ammonium salt of alginic acid | Solvent | | | | | | | |
|---|---|---|---|---|---|---|---|---|
| | | Aqueous ethanol solution | | | | | | |
| | Ethanol | 90% ethanol | 80% ethanol | 70% ethanol | 60% ethanol | 50% ethanol | Methanol | Iso-propanol |
| Dodecyl trimethyl ammonium salt | O | O | O | O | O | O | O | O |
| Tetradecyl dimethyl benzyl ammonium salt | O | O | O | O | O | X | O | O |
| Cetyl pyridinium salt | X | X | O | X | X | X | O | X |
| Benzethonium salt | O | O | O | O | O | X | O | X |
| Methylbenzethonium salt | O | O | O | O | O | X | O | X |

X insoluable
O soluble

Bactericidal Test for Quaternary Ammonium Salts of Alginic Acid (coating)

The quaternary ammonium salts of alginic acid prepared in the foregoing example were tested for bactericidal effect.

A coating of each of the salts was formed on the inner surface of a glass test tube, 18 mm in inside diameter and 180 mm in length, by dissolving a 0.25 g portion of the salt in 3 ml of methanol, applying the solution to the inner surface of the tube to form a uniform thin film thereon and evaporating off the methanol in a vacuum. The test tubes thus prepared and a blank test tube (untreated) were used for bactericidal test. A suspension of *Escherichia coli,* $10^6$ per ml, was placed into each test tube, and the viable count was determined 30 minutes thereafter by the agar plate dilution method. The viable count remained almost unchanged in the case of the untreated tube. The counts in the coated tubes were as follows.

| | Viable count |
|---|---|
| Tetradecyl dimethyl benzyl ammonium salt | 0 |
| Dodecyl trimethyl ammonium salt | 0 |
| Cetyl pyridinium salt | 0 |
| Benzethonium salt | 0 |
| Methylbenzethonium salt | 0 |

Fungicidal Test for Quaternary Ammonium Salt of Alginic Acid (coating)

A test piece was prepaed by coating a 3 cm square plate of slate with the acrylic emulsion coating composition described below. About 10% solution of the tetradecyldimethylbenzylammonium alginate, obtained in the foregoing example, in methanol was sprayed onto the coated surface of the test piece, and the methanol was then evaporated off to form a coating of the quaternary ammonium salt.

The test piece thus obtained and another test piece uncoated with the salt, i.e. a blank, were used for fungicidal test. The test piece was placed on a potato dextrose-agar culture medium at the center, and the medium was inoculated by spraying with a spore suspension of four kinds of fungii, namely, *Aspergillus niger* ATCC 6275, *Aspergillus flavus* ATCC 9643, *Penicillium*

*luteum* ATCC 9644 and *Trichoderma* T-1 ATCC 9645 (prepared based on JIS Z-2911-1981), followed by incubation at 30° C.

The result is shown in Table 2, which reveals that the coating of the quaternary ammonium salt was free of the growth of fungi.

TABLE 2

| Day | Fungicidal effect | |
|---|---|---|
|  | Coated | Blank |
| 7th | 1 | 3 |
| 14th | 1 | 5 |
| 21st | 1 | 5 |

Note: The numbers listed represent the following states of the test piece surface.
1: No growth of fungi on the surface.
2: Slight growth of fungi on the surface.
3: Growth of fungi over ⅓ of the surface.
4: Growth of fungi over ⅔ of the surface.
5: Growth of fungi over the entire surface.

Coating composition:

Preparation from an acrylic emulsion composed of 70 parts of ethyl acrylate and 30 parts of methyl methacrylate, by admixing a thickener, clay, talc, sodium tripolyphosphate, surfactant, etc. with the emulsion and further adding a pigment and paste to the resulting mixture.

Fungicidal Test for Quaternary Ammonium Salt of Alginic Acid (impregnation)

This test was conducted according to JIS Z-2911-1981 Fungus Resistance Test Method, using *Aspergillus niger* ATCC 6275.

The tetradecyl dimethyl benzyl ammonium salt of alginic acid prepared in Preparation Example 1 was dissolved in methanol, and filter paper, 50 mm×50 mm was impregnated with the solution and then dried. In this way, the samples listed in Table 3 were prepared.

The sample was placed on a plate culture medium, 1 ml of spore suspension was uniformly sprinkled over the sample, and the container was closed with a lid, followed by incubation at 30° C. for 2 weeks.

The results are give in Table 4 and the criteria for the evaluation of fungicidal effect in Table 5.

TABLE 3

| Sample No. | Amount of applied salt (g/m²) |
|---|---|
| 1 | 0 |
| 2 | 0.203 |
| 3 | 0.412 |
| 4 | 2.12 |
| 5 | 5.34 |

TABLE 4

| Bacterium | Sample No. | Fungicidal effect |
|---|---|---|
| *Aspergillus* | 1 | 1 |
| *niger* ATCC | 2 | 2 |
| 6275 | 3 | 3 |
|  | 4 | 3 |

TABLE 4-continued

| Bacterium | Sample No. | Fungicidal effect |
|---|---|---|
|  | 5 | 3 |

TABLE 5

| Criteria for evaluation of fungicidal effect | |
|---|---|
| Growth of mycelia | Fungicidal effect |
| No growth of mycelia on the inoculated portion of sample. | 3 |
| Area of growth of mycelia on the inoculated portion of sample was up to ⅓ of the entire area. | 2 |
| Area of growth of mycelia on the inoculated portion of sample exceeded ⅓ of the entire area. | 1 |

The spore suspension was prepared by incubating the test fungus on a potato-agar slant culture medium and dispersing the spores in a sterilized water containing 0.005% of dioctyl sodium sulfosuccinate.

The composition of the plate culture medium was as follows.

| Purified water | 1000 ml |
|---|---|
| Ammonium nitrate | 3.0 g |
| Potassium phosphate, monobasic | 1.0 g |
| Magnesium sulfate | 0.5 g |
| Potassium chloride | 0.25 g |
| Ferrous sulfate | 0.002 g |
| Agar | 25 g |

PREPARATION EXAMPLE 2

Preparation of quaternary ammonium salts of CMC

To 200 g of 1% aqueous solution of the sodium salt of CMC given below was added the quaternary ammonium compound listed in Table 6 below, in an amount of 10% excess of the equivalent weight, and the mixture was stirred. The resulting precipitate was filtered off, thoroughly washed with water and dried in a vacuum at room temperature. Repeating this procedure, various quaternary ammonium salts of CMC were prepared. Table 6 shows the solubilities of these products.

Quaternary ammonium salts of CMC were prepared in the same manner as above using dimethyl distearyl ammonium chloride as the quaternary ammonium compound. When the CMC used was 2.84 in DS, the product was soluble in hydrocarbons such as benzene.

| (1) Sodium salts of CMC used | | |
|---|---|---|
| DS | DP | Viscosity of 1% aqueous solution (cps) |
| 1.27 | 1000 | 1752 |
| 1.37 | 1000 | 1724 |
| 1.46 | 1050 | 1820 |
| 1.50 | 1100 | 2000 |
| 1.58 | 980 | 1600 |
| 1.94 | 550 | 276 |
| 2.41 | 480 | 203 |
| 2.84 | 250 | 84 |

TABLE 6

| Quaternary ammonium compound | Solvent | DS of CMC Sodium | | | | |
|---|---|---|---|---|---|---|
|  |  | 1.27 | 1.37 | 1.46 | 2.41 | 2.84 |
| Lauryl pyridinium chloride | Water | X | X | X | X | X |
|  | Methanol | X | X | X | X |  |
|  | Ethanol | X | X | X | Δ |  |
|  | IPA | X | X | X |  |  |

TABLE 6-continued

| | | 0.69 | 0.75 | 0.88 | 1.06 | 1.17 |
|---|---|---|---|---|---|---|
| Lauryl trimethyl ammonium chloride | Acetone | X | X | X | X | X |
| | Toluene | X | X | X | X | X |
| | Water | X | X | X | X | X |
| | Methanol | X | X | X | | |
| | Ethanol | X | X | X | | |
| | IPA | X | X | X | | |
| | Acetone | X | X | X | X | X |
| | Toluene | X | X | X | X | X |

| Quaternary ammonium compound | Solvent | DS of CMC Sodium | | | | | | | |
|---|---|---|---|---|---|---|---|---|---|
| | | 1.27 | 1.37 | 1.46 | 1.50 | 1.58 | 1.94 | 2.41 | 2.84 |
| Tetradecyl dimethyl benzyl ammonium chloride | Water | X | X | X | X | X | X | X | X |
| | Methanol | X | Δ | Δ | | | | | |
| | Ethanol | X | X | X | X | | | | |
| | IPA | X | X | X | X | | | | |
| | Acetone | X | X | X | X | X | X | X | X |
| | Toluene | X | X | X | X | X | X | X | X |
| Trioctyl methyl ammonium chloride | Water | X | X | X | X | X | X | X | X |
| | Methanol | X | X | X | X | | | | |
| | Ethanol | X | X | X | X | | | | |
| | IPA | X | X | X | X | Δ | | | X |
| | Acetone | X | X | X | X | X | Δ | | |
| | Toluene | X | X | X | X | X | Δ | | |
| Stearyl trimethyl ammonium chloride | Water | | | X | X | X | X | X | X |
| | Methanol | | | | | | | | |
| | Ethanol | | | X | Δ | | | | X |
| | IPA | | | X | X | X | X | X | X |
| | Acetone | | | X | X | X | X | X | X |
| | Toluene | | | X | X | X | X | X | X |

Note:
X: insoluble,
Δ: partially soluble with gel,
: soluble

PREPARATION EXAMPLE 3

Preparation of quaternary ammonium salts of CMC

To 200 g of 1% aqueous solution of the below-mentioned sodium CMC was added the equivalent weight of aqueous solution of the quaternary ammonium compound given below, and the mixture was stirred. The resulting precipitate was filtered off, thoroughly washed with water and dried in a vacuum at room temperature. In this way, various quaternary ammonium salts of CMC were prepared. Table 7 shows the solubilities of these products. The products, although insoluble in water, were found soluble in lower alcohols.

| (1) Sodium CMC used | | |
|---|---|---|
| DS | Degree of polymerization | Viscosity of 1% aq. soln. (cps) |
| 2.41 | 700 | 610 |

(2) Quaternary ammonium compounds used
Benzethonium chloride
Methylbenzethonium chloride
Cetylpyridinium chloride

TABLE 7

| Quaternary ammonium compound | Solvent | | | | | | |
|---|---|---|---|---|---|---|---|
| | Ethanol | Aqueous ethanol | | | | Methanol | Isopropanol |
| | | 90% | 80% | 70% | 60% | | |
| Benzethonium chloride | | | | Δ | X | | |
| Methylbenzethonium chloride | | | | Δ | X | | |
| Cetyl pyridinium chloride | | | Δ | X | X | | |

Note:
The meanings of the marks , Δ and X are the same as those in Table 6

Bactericidal Test 1 for Quaternary Ammonium Salt of CMC (coating)

Sodium CMC, 2.15 in DS, was reacted with tetradecyl dimethyl benzyl ammonium chloride to obtain the tetradecyldimethylbenzylammonium salt of CMC, which was used to conduct the following experiment.

A coating of the salt was formed on the inner surface of each of glass test tubes, 18 mm in inside diameter and 180 mm in length, by dissolving a 0.25 g portion of the salt in 3 ml of methanol, applying the solution to the inner surface to form a uniform thin film thereon and evaporating off the methanol in a vacuum. The test tubes thus prepared and blank test tubes (untreated) were used for bactericidal test, by placing a suspension, having a specified concentration, of each kind of bacteria listed in Table 8 into the tube and determining the viable count 30 minutes later by the agar plate dilution method. The viable count remained almost unchanged in the case of the untreated tube. The counts in the coated tubes are shown in Table 8.

TABLE 8

| Bacterium (concentration) | Viable count |
|---|---|
| *Escherichia coli* (5.1 × 10$^6$ per ml) | 0 per ml. |

TABLE 8-continued

| Bacterium (concentration) | Viable count |
| --- | --- |
| *Staphylocuccus aureus* (7.2 × 10$^6$ per ml) | 0 |
| *Serratia marcescens* (4.0 × 10$^6$ per ml) | 0 |

Bactericidal Test 2 for Quaternary Ammonium Salt of CMC (coating)

The tetradecyldimethylbenzylammonium salt of CMC obtained in the preceding Test 1 was dissolved in methanol, the solution was applied uniformly to the inner surface of a 2-liter glass container, and the methanol was thereafter evaporated off in a vacuum to form a coating. One liter of ion-exchanged water was placed into each of the coated glass container and the same container as above which was not coated (blank), then allowed to stand at 30° C. in a constant-temperature chamber and checked for the viable count of the water by the agar plate dilution method using a standard agar culture medium. Table 9 shows the result. The water in the coated glass container was found to remain free from bacteria over a long period of time when the testing procedure was repeated.

TABLE 9

|  |  | Coated | Blank (uncoated) |
| --- | --- | --- | --- |
| 1st | After 30 mins | 0 per ml | 2.3 × 10 per ml |
|  | After 1 day | 0 | 2.5 × 10$^2$ |
|  | After 3 days | 0 | 2.6 × 10$^4$ |
|  | After 5 days | 0 | 3.0 × 10$^4$ |
| 2nd | After 30 mins | 0 | 9 |
|  | After 1 day | 0 | 1.8 × 10 |
|  | After 3 days | 0 | 8.1 × 10$^3$ |
|  | After 5 days | 0 | 5.3 × 10$^4$ |
| 3rd | After 30 mins | 0 | 4.2 × 10 |
|  | After 3 days | 0 | 9.2 × 10$^2$ |
|  | After 7 days | 0 | 2.5 × 10$^5$ |
|  | After 14 days | 0 | 3.7 × 10$^5$ |

Fungicidal Test for Quaternary Ammonium Salt of CMC (coating)

A test piece was prepared by coating a 3 cm square plate of slate with the same acrylic emulsion coating composition as used above. A solution of the tetradecyldimethylbenzylammonium salt of CMC, prepared in CMC salt Bactericidal Test 1, in methanol was sprayed onto the coated surface of the test piece, and the methanol was then evaporated off to form a coating of the quaternary ammonium salt of CMC.

The test piece thus obtained and another test piece uncoated with the salt, i.e. a blank, were used for fungicidal test. The test piece was placed on a potato dextrose-agar culture medium at the center, and the medium was inoculated by spraying with a spore suspension of four kinds of fungii, namely, *Aspergillus niger* ATCC 6275, *Aspergillus flavus* ATCC 9643, *Penicillium luteum* ATCC 9644 and *Trichoderma* T-1 ATCC 9645 (prepared based on JIS Z-2911-1981), followed by incubation at 30° C. to observe growth of the fungi. The result is given in Table 10, which reveals that the coating of the quaternary ammonium salt of CMC was free of the growth of fungi.

TABLE 10

| | Fungicidal effect | |
| --- | --- | --- |
| Day | Coated | Blank |
| 7th | 1 | 3 |
| 14th | 1 | 5 |
| 21st | 1 | 5 |

Note: The numbers listed represent the same meaning as in Table 2.

Bactericidal Test 3 for Quaternary Ammonium Salts of CMC (coating)

The tetradecyldimethylbenzylammonium salt and dodecyltrimethylammonium salt of CMC were prepared by reacting sodium CMC, 2.15 in DS, with tetradecyl dimethyl benzyl ammonium chloride or with dodecyl trimethyl ammonium chloride. Further the cetylpyridinium salt, benzethonium salt and methylbenzethonium salt of CMC were prepared by reacting sodium CMC, 2.41 in DS, with cetyl pyridinium chloride, benzethonium chloride or methyl benzethonium chloride. These salts were used to conduct the following experiment.

A coating of each of the salts was formed on the inner surface of a glass tube, 18 mm in inside diameter and 180 mm in length, by dissolving a 0.25 g portion of the salt in 3 ml of methanol, applying the solution to the inner surface to form a uniform thin film thereon and evaporating off the methanol in a vacuum. The test tubes thus prepared and a blank test tube (untreated) were used for bactericidal test. A suspension of *Escherichia coli*, 10$^6$ per ml, was placed into each tube, and the viable count was determined 30 minutes later by the agar plate dilution method. The number of cells remained almost unchanged in the case of the untreated tube. The counts in the coated tubes were as follows.

| CMC salt | Viable count |
| --- | --- |
| Tetradecyldimethylbenzylammonium salt | 0 per ml |
| Dodecyltrimethylammonium salt | 0 |
| Cetylpyridinium salt | 0 |
| Benzethonium salt | 0 |
| Methylbenzethonium salt | 0 |

Fungicidal Test for Quaternary Ammonium Salt of CMC (impregnation)

This test was conducted according to JIS Z-2911-1981, Fungus Resistance Test Method, using *Aspergillus niger* and *Penicillium funiculosum*. The tetradecyl dimethyl benzyl ammonium salt of CMC (DS 2.41) prepared in Preparation Example 2 was dissolved in ethanol, and filter paper, 50 mm×50 mm, was impregnated with the solution and then dried. In this way, the samples listed in Table 11 were prepared.

The sample was placed on a plate culture medium, 1 ml of a spore suspension was uniformly sprinkled over the sample, and the container was closed with a lid, followed by incubation at 30° C. for 2 weeks.

The results are given in Table 12, and the criteria for the evaluation of fungicidal effect in preceding Table 5.

The spore suspension and composition of the plate culture medium are the same as those in "Fungicidal Test for Quaternary Ammonium Salt of Alginic Acid (impregnation)".

TABLE 11

| Sample No. | Amount of applied salt (g/m²) |
|---|---|
| 1 | 0 |
| 2 | 0.196 |
| 3 | 0.392 |
| 4 | 1.96 |
| 5 | 3.92 |
| 6 | 8.16 |

TABLE 12

| Bacterium | Sample No. | Fungicidal effect |
|---|---|---|
| Aspergillus | 1 | 1 |
| niger | 2 | 2 |
| ATCC 6275 | 3 | 3 |
|  | 4 | 3 |
|  | 5 | 3 |
|  | 6 | 3 |
| Penicillium | 1 | 1 |
| funiculosum | 2 | 1 |
| FERM S-6 | 3 | 3 |
|  | 4 | 3 |
|  | 5 | 3 |
|  | 6 | 3 |

What is claimed is:

1. A method of imparting fungicidal and bactericidal properties to an article which comprises coating or impregnating the article with a solution of a fungicidal and bactericidal quaternary ammonium salt in an organic solvent or a mixture of the organic solvent and a small amount of water and thereafter removing the solvent from the article, the quaternary ammonium salt being insoluble or sparingly soluble in water and represented by the formula (I)

$$X^{(-)}R^4-\overset{R^1}{\underset{R^3}{\overset{|(+)}{N}}}-R^2 \qquad (I)$$

wherein $X^{(-)}$ is a group formed by removing a hydrogen ion from at least one carboxyl group of alginic acid or carboxymethylcellulose having 1.5–3.0 as the degree of substitution by carboxymethyl group per anhydrous glucose unit; and $R^1$ to $R^4$ are each a $C_{1-20}$ straight-chain or branched saturated or unsaturated aliphatic hydrocarbon group, three of $R^1$ to $R^4$ are each the hydrocarbon group and the remaining one is an aralkyl group, a trialkylammoniumalkyl group or an aryloxyalkyl group, two of $R^1$ to $R^4$ are each the hydrocarbon group and the remaining two are an aralkyl group and a dialkylpheoxy- or alkylphenoxy-alkyleneoxyalkyl group, or one or two of $R^1$ to $R^4$ are the hydrocarbon group and the remaining two or three form a heterocyclic ring together with the nitrogen atom.

2. The method according to claim 1 wherein the quaternary ammonium salt is tetradecyl dimethyl benzyl ammonium salt, dodecyl trimethyl ammonium salt, cetylpyridinium salt, benzethonium salt or methylbenzethonium salt of alginic acid or carboxymethyl cellulose.

3. The method according to claim 1 wherein the organic solvent is a lower alkyl alcohol selected from the group consisting of methanol, ethanol, propanol or isopropanol, or acetone or toluene.

4. The method according to claim 1 wherein the concentration of the quaternary ammonium salt in the solvent is 0.01 to 30 (W/V) %.

5. An article having fungicidal and bactericidal properties, said article being coated or impregnated with a quaternary ammonium salt that is insoluble or sparingly soluble in water and is represented by the formula (I):

$$X^{(-)}R^4-\overset{R^1}{\underset{R^3}{\overset{|(+)}{N}}}-R^2 \qquad (I)$$

wherein $X^{(-)}$ is a group formed by removing a hydrogen ion from at least one carboxyl group of alginic acid or carboxymethylcellulose having 1.5–3.0 as the degree of substitution by carboxymethyl group per anhydrous glucose unit; and $R^1$ to $R^4$ are each a $C_{1-20}$ straightchain or branched saturated or unsaturated aliphatic hydrocarbon group, three of $R^1$ to $R^4$ are each the hydrocarbon group and the remaining one is an aralkyl group, a trialkylammoniumalkyl group or an aryloxyalkyl group, two of $R^1$ to $R^4$ are each the hydrocarbon group and the remaining two are an aralkyl group and a dialkylphenoxy- or alkylphenoxy-alkyleneoxyalkyl group, or one or two of $R^1$ to $R^4$ are the hydrocarbon group and the remaining two or three form a heterocyclic ring together with the nitrogen atom.

6. The article according to claim 5, wherein the quaternary ammonium salt is tetradecyl dimethyl benzyl ammonium salt, dodecyl trimethyl ammonium salt, cetyl-pyridinium salt, benzethoniumsalt or methylbenzethonium salt of alginic acid or carboxymethyl cellulose.

* * * * *

UNITED STATES PATENT AND TRADEMARK OFFICE
CERTIFICATE OF CORRECTION

PATENT NO. :  4,877,617                                    Page 1 of 5
DATED      :  October 31, 1989
INVENTOR(S):  HAJIME NAMIKOSHI et al.

It is certified that error appears in the above-identified patent and that said Letters Patent is hereby corrected as shown below:

Column 1, line 55:   Change "notnIng" to --nothing--.

Column 3, line 41:   Change "exwmples" to --examples--.

Column 3, line 49:   Change "salts" to --salt--.

Column 5, line 44:   Change "on" to --no--.

Column 6, Bottom of Table 1:  Change "insoluable" to --insoluble--.

Column 6, line 54:   Change "prepaed" to --prepared--.

Column 7, line 21:   Change "Preparation" to --Prepared--.

Column 7, line 42:   Change "give" to --given--.

Columns 8-9, Table 6:

UNITED STATES PATENT AND TRADEMARK OFFICE
CERTIFICATE OF CORRECTION

PATENT NO. : 4,877,617

DATED : October 31, 1989

INVENTOR(S) : HAJIME NAMIKOSHI ET AL

It is certified that error appears in the above-identified patent and that said Letters Patent is hereby corrected as shown below:

Table 6 should read as follows:

Table 6a

| Quaternary ammonium compound | Solvent | DS of CMC Sodium | | | | |
|---|---|---|---|---|---|---|
| | | 1.27 | 1.37 | 1.46 | 2.41 | 2.84 |
| Lauryl pyridinium chloride | Water | X | X | X | X | X |
| | Methanol | X | X | X | X | O |
| | Ethanol | X | X | X | △ | O |
| | IPA | X | X | X | O | O |
| | Acetone | X | X | X | X | X |
| | Toluene | X | X | X | X | X |
| Lauryl trimethyl ammonium chlovide | Water | X | X | X | X | X |
| | Methanol | X | X | X | O | O |
| | Ethanol | X | X | X | O | O |
| | IPA | X | X | X | O | O |
| | Acetone | X | X | X | X | X |
| | Toluene | X | X | X | X | X |

UNITED STATES PATENT AND TRADEMARK OFFICE
CERTIFICATE OF CORRECTION

PATENT NO. : 4,877,617
DATED : October 31, 1989
INVENTOR(S) : HAJIME NAKIKOSHI et al.

It is certified that error appears in the above-identified patent and that said Letters Patent is hereby corrected as shown below:

Table 6b

| Quaternary ammonium compound | Solvent | DS of CMC Sodium | | | | | | | |
|---|---|---|---|---|---|---|---|---|---|
| | | 1.27 | 1.37 | 1.46 | 1.50 | 1.58 | 1.94 | 2.41 | 2.84 |
| Tetradecyl dimethyl benzyl ammonium chloride | Water | X | X | X | X | X | X | X | X |
| | Methanol | X | △ | △ | O | O | O | O | O |
| | Ethanol | X | X | X | X | O | O | O | O |
| | IPA | X | X | X | X | O | O | O | O |
| | Acetone | X | X | X | X | X | X | X | X |
| | Toluene | X | X | X | X | X | X | X | X |
| Trioctyl methyl ammonium chloride | Water | X | X | X | X | X | X | X | X |
| | Methanol | X | X | X | X | O | O | O | O |
| | Ethanol | X | X | X | X | O | O | O | O |
| | IPA | X | X | X | X | △ | O | O | X |
| | Acetone | X | X | X | X | X | △ | O | O |
| | Toluene | X | X | X | X | X | △ | O | O |

Table 6c

| Quaternary ammonium compound | Solvent | DS of CMC Sodium | | | | | | | |
|---|---|---|---|---|---|---|---|---|---|
| | | 1.27 | 1.37 | 1.46 | 1.50 | 1.58 | 1.94 | 2.41 | 2.84 |
| Stearyl trimethyl ammonium chloride | Water | | | X | X | X | X | X | X |
| | Methanol | | | O | O | O | O | O | O |
| | Ethanol | | | X | △ | O | O | O | X |
| | IPA | | | X | X | X | X | X | X |
| | Acetone | | | X | X | X | X | X | X |
| | Toluene | | | X | X | X | X | X | X |

Note: X: insoluble, △: partially soluble with gel, O: soluble

UNITED STATES PATENT AND TRADEMARK OFFICE
CERTIFICATE OF CORRECTION

PATENT NO. : 4,877,617

DATED : October 31, 1989

INVENTOR(S) : HAJIME NAMIKOSHI et al

It is certified that error appears in the above-identified patent and that said Letters Patent is hereby corrected as shown below:

Column 9, Table 7 should read as follows:

Table 7

| Solvent / Quaternary ammonium compound | Ethanol | Aqueous ethanol | | | | Methanol | Isopropanol |
|---|---|---|---|---|---|---|---|
| | | 90% | 80% | 70% | 60% | | |
| Benzethonium chloride | ○ | ○ | ○ | △ | X | ○ | ○ |
| Methylbenzethonium chloride | ○ | ○ | ○ | △ | X | ○ | ○ |
| Cetyl pyridinium chloride | ○ | ○ | △ | X | X | ○ | ○ |

Note : The meanings of the marks ○, △ and X are the same as those in Table 6

UNITED STATES PATENT AND TRADEMARK OFFICE
CERTIFICATE OF CORRECTION

PATENT NO. : 4,877,617

DATED : October 31, 1989

INVENTOR(S) : HAJIME NAMIKOSHI ET AL

It is certified that error appears in the above-identified patent and that said Letters Patent is hereby corrected as shown below:

Column 13, line 25: Claim 1, line 1, after "imparting" insert --water resistant improved--.

Column 14, line 47: Change "benzethoniumsalt" to --benzethonium salt--.

Signed and Sealed this

Third Day of March, 1992

Attest:

HARRY F. MANBECK, JR.

Attesting Officer

Commissioner of Patents and Trademarks